United States Patent
Shams

(10) Patent No.: US 9,066,850 B2
(45) Date of Patent: Jun. 30, 2015

(54) ENTERAL FEEDING DEVICES, BUTTONS, AND/OR CONNECTORS

(71) Applicant: Iden Shams, Richmond (GB)

(72) Inventor: Iden Shams, Richmond (GB)

(*) Notice: Subject to any disclaimer, the term of this patent is extended or adjusted under 35 U.S.C. 154(b) by 0 days.

(21) Appl. No.: 13/937,957

(22) Filed: Jul. 9, 2013

(65) Prior Publication Data

US 2014/0018777 A1    Jan. 16, 2014

(30) Foreign Application Priority Data

Jul. 12, 2012 (GB) .................................. 1212443.4

(51) Int. Cl.
| | |
|---|---|
| *A61M 25/16* | (2006.01) |
| *A61J 15/00* | (2006.01) |
| *A61M 39/10* | (2006.01) |
| A61M 25/02 | (2006.01) |

(52) U.S. Cl.
CPC .......... *A61J 15/0015* (2013.01); *A61J 15/0057* (2013.01); *A61J 15/0026* (2013.01); *A61M 39/1011* (2013.01); *A61M 2025/0233* (2013.01); *A61M 2039/1027* (2013.01)

(58) Field of Classification Search
CPC ... A61J 15/0015; A61J 15/0026; A61J 15/00; A61J 15/0057; A61J 15/0061; A61J 15/0069; A61B 17/3415; A61M 2202/0482; A61M 39/10

USPC .................................................. 604/533, 910
See application file for complete search history.

(56) References Cited

U.S. PATENT DOCUMENTS

| | | | | |
|---|---|---|---|---|
| 5,716,347 | A * | 2/1998 | Gibbs et al. .................... | 604/247 |
| 6,019,746 | A * | 2/2000 | Picha et al. .................... | 604/175 |
| 8,048,062 | B2 * | 11/2011 | Adams et al. ................. | 604/535 |
| 2010/0185159 | A1 * | 7/2010 | Bagwell et al. ............... | 604/256 |

FOREIGN PATENT DOCUMENTS

| | | |
|---|---|---|
| WO | WO01/60313 A1 | 8/2001 |
| WO | WO2011/077286 A1 | 6/2011 |

* cited by examiner

*Primary Examiner* — Nicholas Lucchesi
*Assistant Examiner* — Diva K Chander
(74) *Attorney, Agent, or Firm* — Muncy, Geissler, Olds & Lowe, P.C.

(57) ABSTRACT

An enteral feeding device comprises a connector with a tube for establishing a fluid connection between the connector and a button; the enteral feeding device incorporating a button with an aperture; the connector's tube incorporating an ear projecting laterally from the tube; the button's aperture being substantially circular with a recessed portion sized and shaped to allow the connector's ear to be inserted into the button; wherein the button's aperture further incorporates at least one inwardly projecting ear; and the connector's tube incorporates at least one recessed channel for receiving the at least one ear during the connection of the tube to the button.

7 Claims, 6 Drawing Sheets

ENTERAL FEEDING DEVICES, BUTTONS, AND/OR CONNECTORS

CLAIM OF PRIORITY UNDER 35 U.S.C. §119

This nonprovisional application claims priority under 35 U.S.C. §119(a) to United Kingdom Patent Application No. GB1212443.4, which was filed in the United Kingdom on Jul. 12, 2012, and which is herein incorporated by reference.

FIELD OF DISCLOSURE

The present disclosure relates to enteral feeding devices, enteral buttons and/or enteral connectors.

BACKGROUND

Conventional enteral feeding through gastrostomy button devices comprise a connector with a tube for establishing a fluid connection between a connector and the gastrostomy button. This system has been extensively used as a standard form of connection for many years. One of the difficulties with a standard port on the buttons is that a Luer syringe can be readily connected to it. In the past few years, there has been a realization that, due to the possibility of misconnections and wrong route injection of medicines and other fluids, Luer connections should only be used for intravenous injection. Feeding the erroneous contents to a patient via a button may readily occur due to the widespread use of Luer connections. Furthermore, there is a need to improve the connections between connectors and buttons in addition to providing a safe connection mechanism.

SUMMARY

In a first broad independent aspect, the present disclosure provides an enteral feeding device particularly suited for gastrostomy comprising a connector with a tube for establishing a fluid connection between the connection and the button; the enteral feeding device incorporating a button with an aperture; the connector's tube incorporating an ear projecting laterally from the tube; the tube's aperture being substantially circular with a recessed portion sized and shaped to allow the connector's ear to be inserted into the button; wherein the button's aperture further incorporates at least one inwardly projecting ear; and the connector's tube incorporates at least one recessed channel for receiving the at least one ear during the connection of the tube to the button.

This configuration is particularly advantageous since it allows the connection to be a non-Luer connection whilst at the same time providing improvements to the fitment of the connector to the button. In other words, a Luer device is incompatible with the button. It also allows the operators to follow the same mode of assembly—there is therefore no requirement for operator training for the new safe connection of the connector to the button.

In a subsidiary aspect, the tube incorporates diametrically oppositely disposed recessed channels and the button's aperture incorporates two diametrically oppositely disposed ears. This configuration provides an accurate guide for the connector to be inserted into the button whilst preventing potentially non-feed related equipment (such as a Luer syringe) being used. In this configuration, the fit between co-operating parts is also particularly tight and secure.

In a further subsidiary aspect, the button incorporates a partially annular ramp for guiding the connector's ear between a first position where the ear is inserted in the button's recessed portion and a second position where the tube's ear rests against an abutment after the connector has been rotated relative to the button.

This configuration is particularly advantageous because it allows a controlled rotation for in effect locking the connector onto the button.

In a further subsidiary aspect, the connector's tube incorporates a tapered distal portion below said recessed channel and the ear for establishing a fluid tight connection with a corresponding portion of the button.

This configuration is particularly advantageous because it provides not only a secure attachment of the components but a fluid tight connection.

In a second broad independent aspect, the present disclosure provides an enteral button comprising an aperture which is substantially circular with a laterally extending recessed portion; wherein the button's aperture further incorporates at least one inwardly projecting ear.

This configuration is particularly advantageous in terms of preventing a standard Luer connection taking place whilst at the same time providing a simplification of the alignment requirements when inserting the connector into the button.

In a subsidiary aspect, the button comprises a partially annular ramp provided between the recessed portion and an abutment. This combination of features further improves the efficiency of securing the connector to the button.

In a third broad independent aspect, the present disclosure provides an enteral connector comprising a tube for establishing a fluid connection with a button; the tube incorporating an ear projecting laterally from the tube; and an external recessed channel extending longitudinally. This further improves the alignment between connector and button in order to simplify the assembly of these components whilst at the same time removing the possibility of inserting a standard Luer connection into the aperture of a button.

BRIEF DESCRIPTION OF THE DRAWINGS

The accompanying drawings are presented to aid in the description of embodiments of the invention and are provided solely for illustration of the embodiments and not limitation thereof.

DETAILED DESCRIPTION

Aspects of the invention are disclosed in the following description and related drawings directed to specific embodiments of the invention. The term "embodiments of the invention" does not require that all embodiments of the invention include the discussed feature, advantage, or mode of operation, and alternate embodiments may be devised without departing from the scope of the invention. Additionally, well-known elements of the invention may not be described in detail or may be omitted so as not to obscure more relevant details of the invention.

Figure 1:
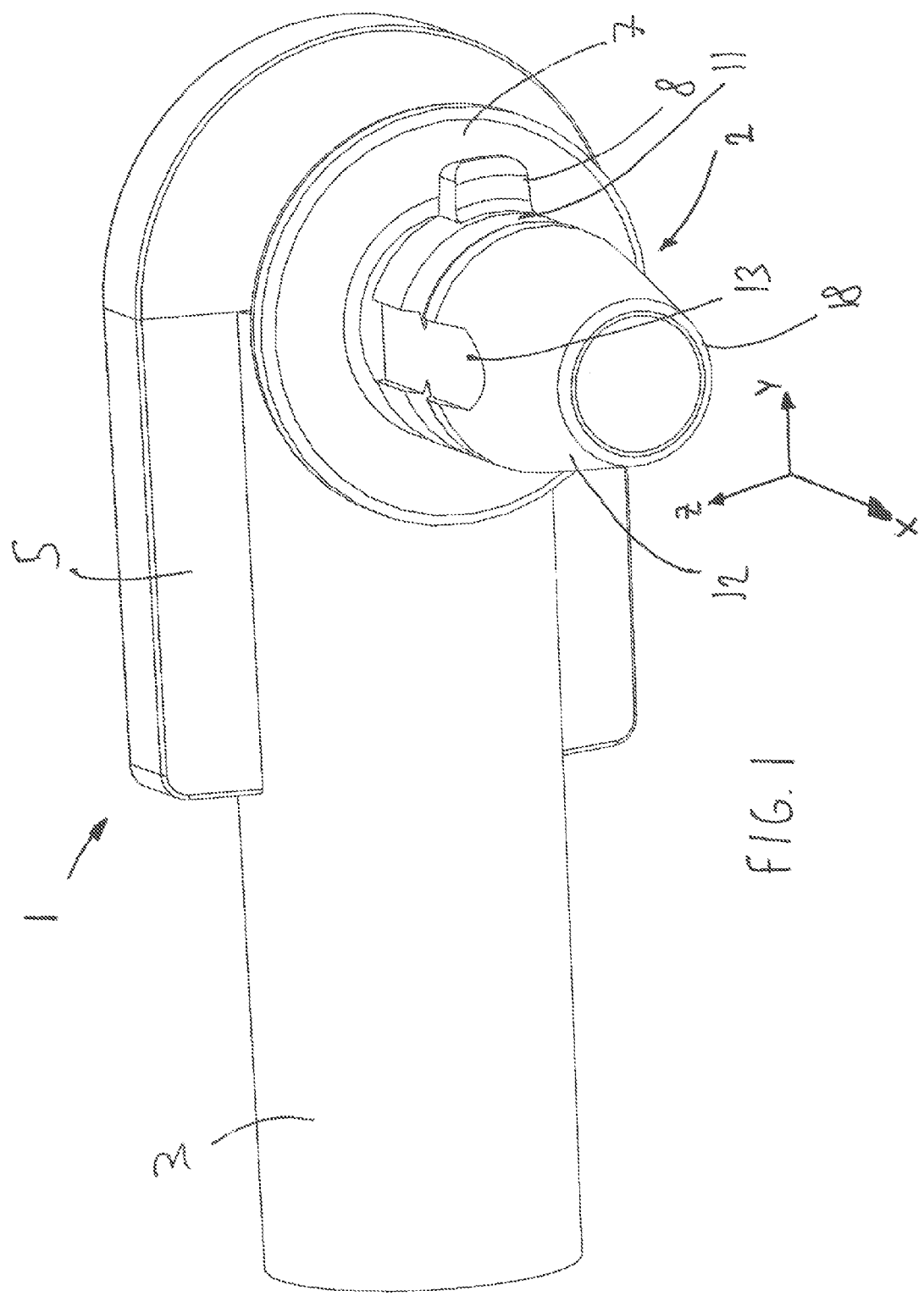
FIG. 1 shows a perspective view from below of an enteral connector prior to assembly with a button.

FIG. 1 shows a connector 1 with a tube 2 for establishing a fluid connection between the connector and an enteral button. An enteral button is described in detail in FIGS. 3 and 4.

Figure 3:
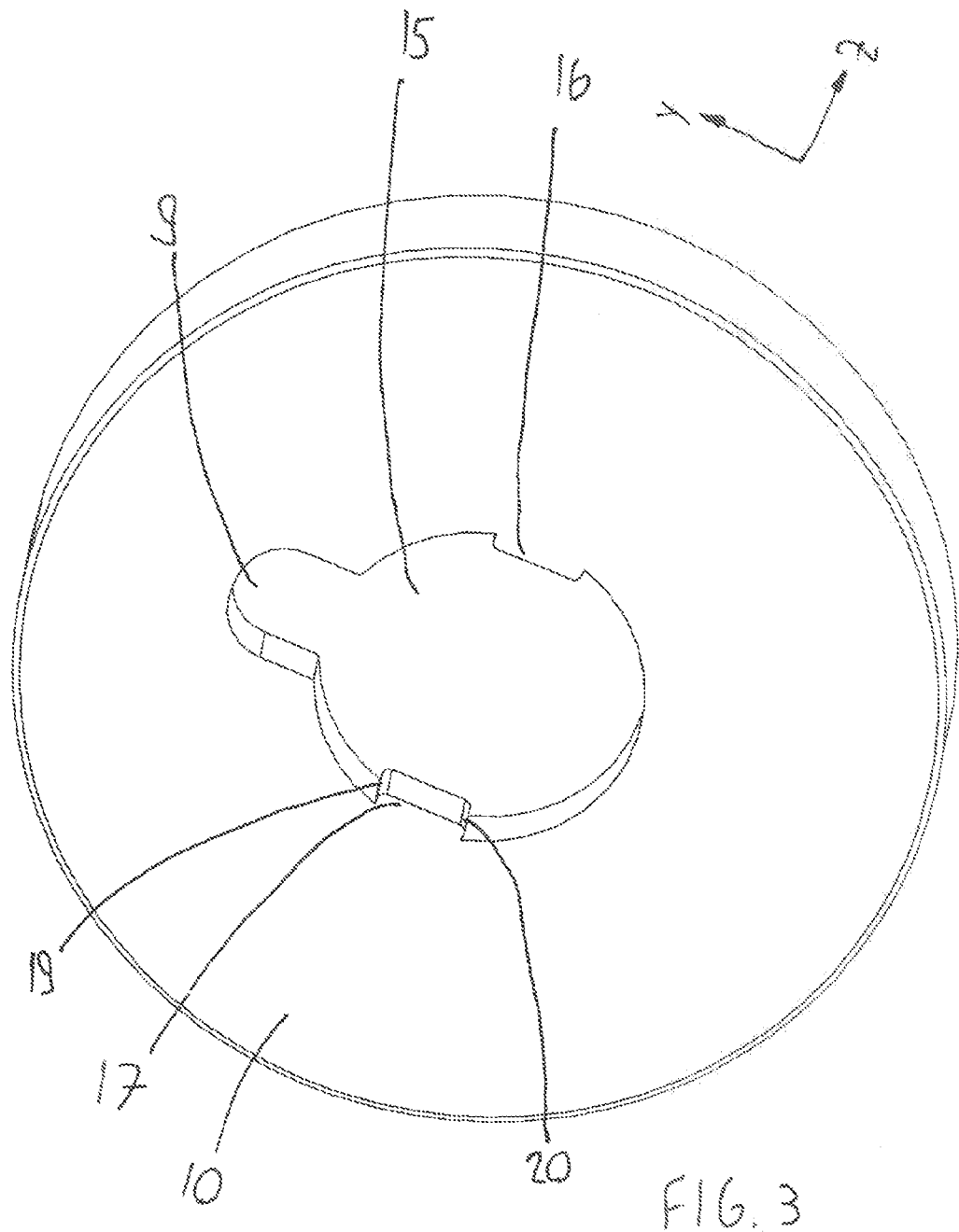
FIG. 3 shows a perspective top view of an enteral button.
Figure 6:
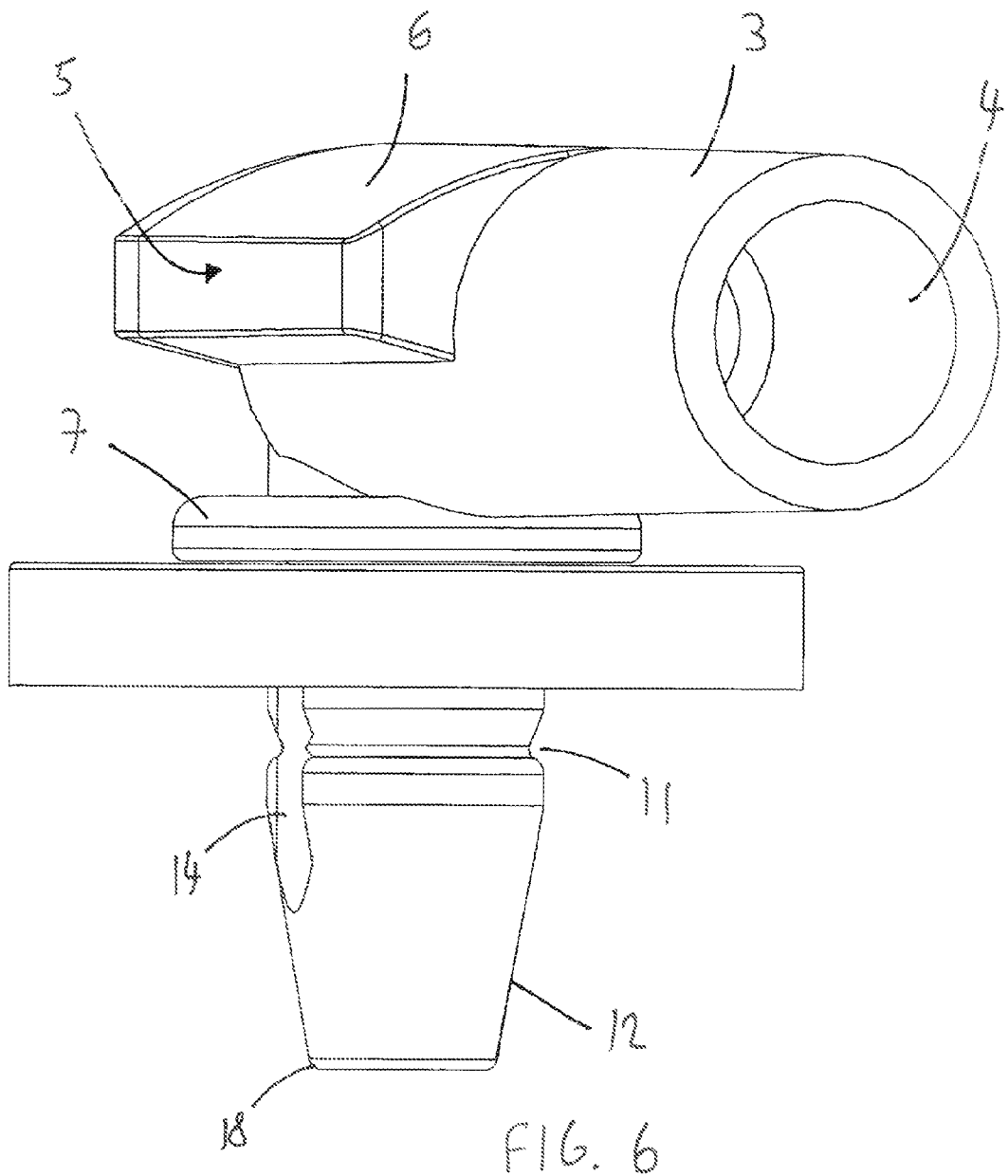
FIG. 6 shows a perspective view of an assembly of a connector with a button.

Connector 1 incorporates a laterally extending duct 3 for connection to appropriate tubing. A bore 4 (as shown in FIG. 6) is provided at its distal extremity. An overhang portion 5 extends radially outwardly beyond the button connecting portion of the connector. Overhang 5 incorporates a substantially domed upper surface 6 (as shown in FIG. 6). The button connecting portion of the connector incorporates an annular member 7 which would sit on the upper surface of a button when assembled (see FIG. 6). The tube 2 extends substantially at a right-angle from duct 3 and is substantially circular in shape. Projecting laterally (in the Y direction), an ear 8 is provided. Ear or peg 8 is sized and shaped to fit and pass through recessed portion 9 (as shown in FIG. 3) of the button 10. A recessed annular portion 11 is provided below ear 8. At the proximal extremity of the tube 2, a tapered portion 12 allows the liquid-tight connection with a corresponding tapered portion in a bore in the button of the enteral feeding device. For clarity, this tapered bore is not shown in the figures.

Figure 2:
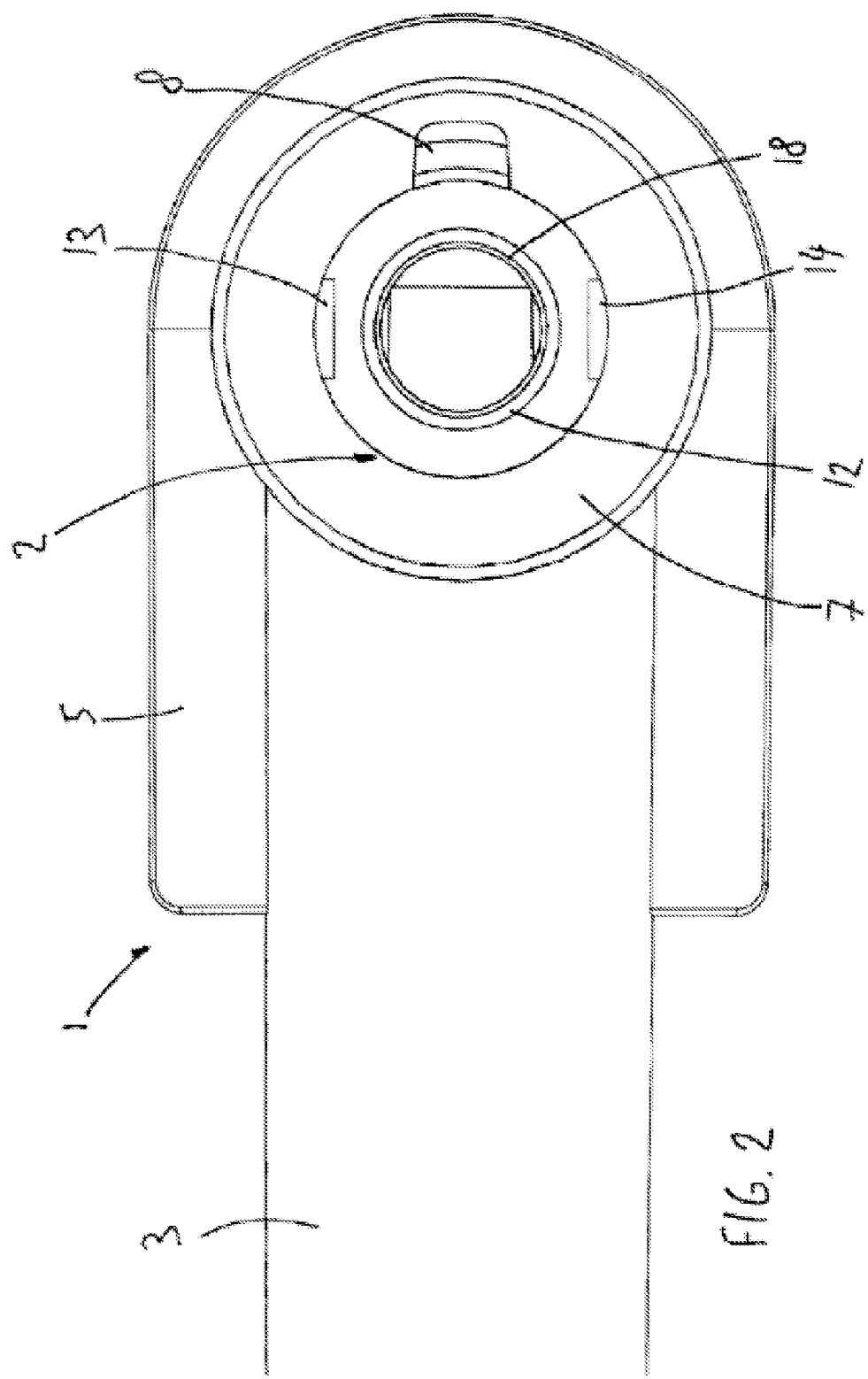
FIG. 2 shows a bottom elevation of an enteral connector.

Two recessed channels 13 and 14 (see FIG. 2) extend in the longitudinal direction (the X direction) of the tube and are disposed diametrically oppositely to one another. These recessed channels are sized and shaped to allow the insertion of tube 2 into aperture 15 of button 10. The recessed channels accommodate two diametrically oppositely disposed ears 16 and 17 as shown in FIG. 3. Beneath the tapered portion 12, a radiused end portion 18 is provided.

Button 10 as shown in the figures represents the upper part of the button portion of an enteral feeding device. The button would naturally incorporate other components, which are not shown since these are standard components which may be found in any prior art enteral feeding devices. Button 10 incorporates an aperture or keyhole 15 with a recessed portion 9 extending radially outwards from the main substantially circular aperture. This recess extends substantially in the Y direction whilst ears 16 and 17 are provided in the Z direction. The central radius of recessed portion 9 is approximately at 90° from the central radius of ear 16. Ears 16 and 17 are disposed diametrically opposite to one another. Whilst ears 16 and 17 are substantially rectangular in shape their lateral edges 19 and 20 are radiused.

Figure 4:
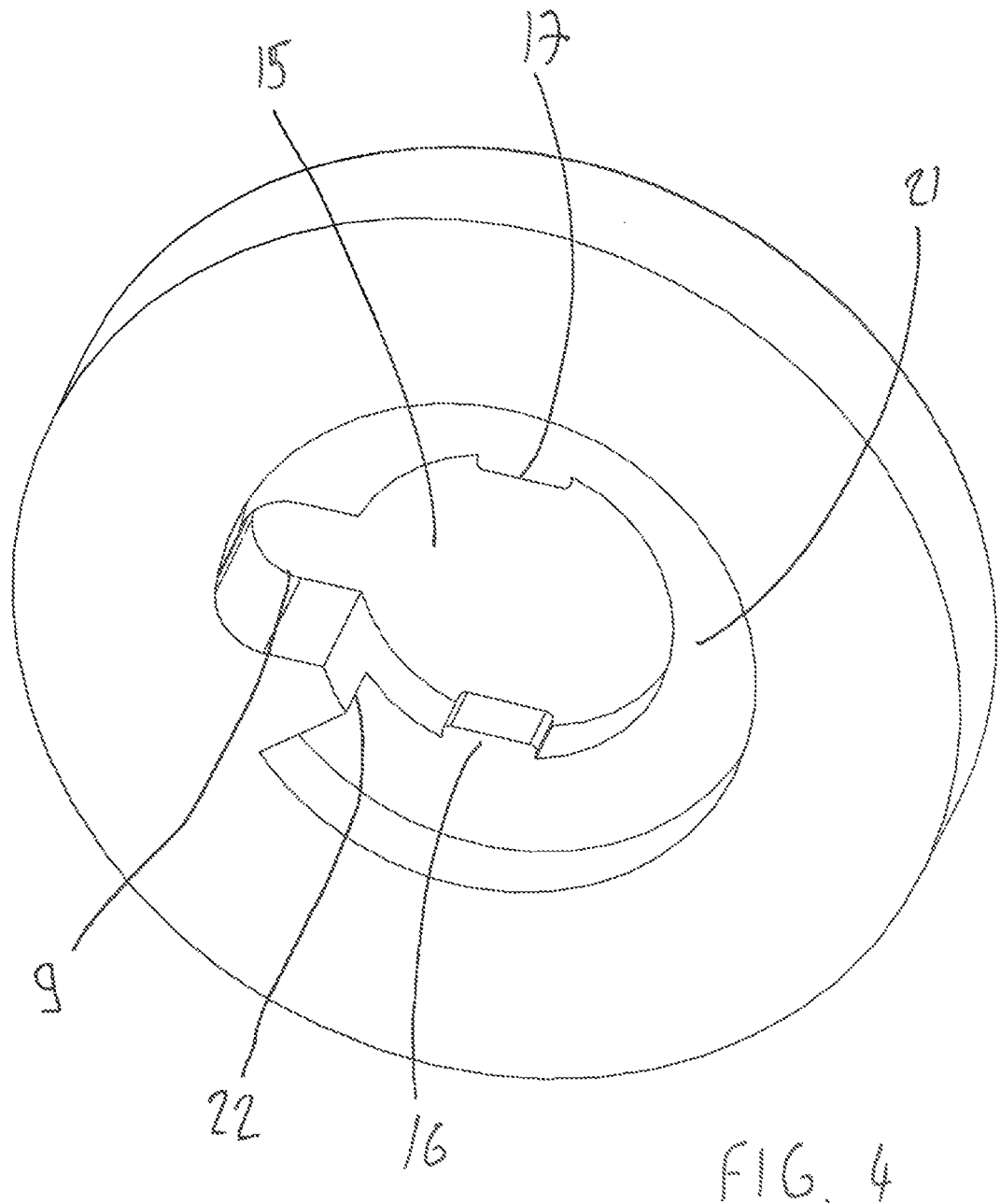
FIG. 4 shows a bottom view of a button.
Figure 5:
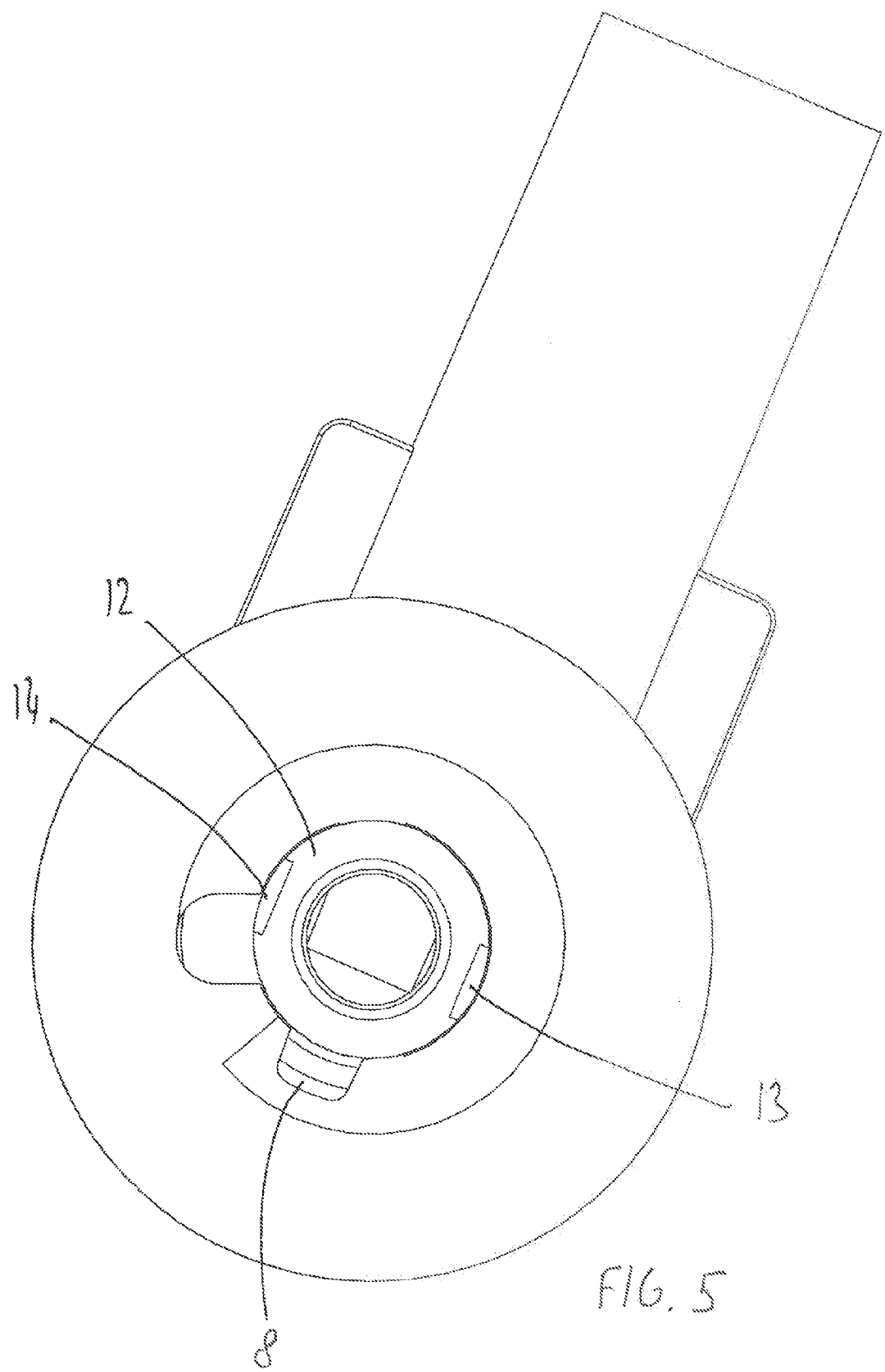
FIG. 5 shows a bottom view of the assembly of an enteral connector and an enteral button.

Referring to FIG. 4, an annular ramp 21 extends from recessed portion 9 to an abutment 22. As shown in FIG. 5, once the connector's tube together with its ear 8 are inserted through aperture 15, ear 8 is initially received in the recessed portion 9 and can run against ramp 21 as the connector is rotated relative to the button until ear 8 reaches abutment 22. FIG. 5 shows ear 8 prior to abutting against surface 22. Ears 16 and 17 are received in a corresponding annular recess located above ear 8 in order to act as a further retention means as the tube 12 is rotated between a first position where the ears 16 and 17 are respectively lodged in their corresponding recessed channels 13 and 14 and a second position where the ears are lodged in an annular recess. In order to detach the connector from its button the tube portion is rotated back to the position where ear 8 is in alignment with recess portion 9 and ears 16 and 17 are in alignment with elongate recessed channels 13 and 14.

The forgoing description is provided to enable any person skilled in the art to make or use embodiments of the present invention. It will be appreciated, however, that the present invention is not limited to the particular formulations, process steps, and materials disclosed herein, as various modifications to these embodiments will be readily apparent to those skilled in the art. That is, the generic principles defined herein may be applied to other embodiments without departing from the spirit or scope of the invention.

The invention claimed is:

1. An enteral feeding device comprising a connector with a tube for establishing a fluid connection between said connector and a button; said enteral feeding device incorporating a button with an aperture; the connector's tube incorporating an ear projecting laterally from said tube; said button's aperture being substantially circular with a recessed portion sized and shaped to allow the connector's ear to be inserted into said button; wherein said button's aperture further incorporates at least one inwardly projecting ear; and said connector's tube incorporates at least one external recessed channel extending longitudinally for receiving said at least one ear during the connection of said tube to said button.

2. An enteral feeding device according to claim 1, wherein said tube incorporates diametrically oppositely disposed recessed channels and said button's aperture incorporates two diametrically oppositely disposed ears.

3. An enteral feeding device according to claim 1, wherein said button incorporates a partially annular ramp for guiding said connector's ear between a first position where the ear is inserted in said button's recessed portion and a second position where said tube's ear rests against an abutment after said connector has been rotated relative to said button.

4. An enteral feeding device according to claim 1, wherein the connector's tube incorporates a tapered distal portion below said recessed channel and said ear for establishing a fluid tight connection with a corresponding portion of said button.

5. An enteral button comprising an upper most portion with an aperture which is substantially circular with a laterally extending recessed portion; wherein said substantially circular aperture incorporates at least one radially inwardly projecting ear.

6. An enteral button according to claim 5, further comprising a partially annular ramp provided between said recessed portion and an abutment.

7. An enteral connector comprising a tube for establishing a fluid connection with a button; said tube incorporating an ear projecting laterally from said tube; and an external recessed channel extending longitudinally.

* * * * *